(12) United States Patent
Yoshida (10) Patent No.: US 7,679,047 B2
(45) Date of Patent: Mar. 16, 2010

(54) INFRARED GAS SENSING APPARATUS AND METHOD

(75) Inventor: Takahiko Yoshida, Okazaki (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 11/896,803

(22) Filed: Sep. 6, 2007

(65) Prior Publication Data

US 2008/0251726 A1 Oct. 16, 2008

(30) Foreign Application Priority Data

Sep. 20, 2006 (JP) ............................. 2006-254716

(51) Int. Cl.
*G01J 5/54* (2006.01)
(52) U.S. Cl. .............................. 250/252.1; 250/339.09; 250/341.5
(58) Field of Classification Search .............. 250/252.1, 250/339.01, 339.06, 339.09, 341.5
See application file for complete search history.

(56) References Cited

U.S. PATENT DOCUMENTS

| | | | | |
|---|---|---|---|---|
| 3,825,756 | A | * | 7/1974 | Weiss .......................... 250/343 |
| 5,451,787 | A | * | 9/1995 | Taylor ....................... 250/338.5 |
| 5,550,373 | A | * | 8/1996 | Cole et al. ................ 250/338.1 |
| 5,561,523 | A | | 10/1996 | Blomberg et al. |
| 5,835,216 | A | | 11/1998 | Koskinen |
| 6,590,710 | B2 | | 7/2003 | Hara et al. |
| 6,843,102 | B1 | | 1/2005 | Shulga et al. |
| 7,286,244 | B2 | | 10/2007 | Murata |
| 2001/0015810 | A1 | | 8/2001 | Hara et al. |
| 2003/0116711 | A1 | * | 6/2003 | Hara et al. ................ 250/338.1 |

FOREIGN PATENT DOCUMENTS

JP A-2003-014641 1/2003

OTHER PUBLICATIONS

Office Action dated Mar. 24, 2009 from the German Patent Office in the corresponding DE Application No. 102007039884.2 (and English Translation).
Office Action dated Mar. 6, 2009 in corresponding Chinese patent application No. 2007101547970 (and English translation).
Office Action mailed on Apr. 28, 2009 issued from the Japanese Patent Office for the corresponding Japanese patent application No. 2006- 254716 (and English translation).
Haruyuki Hisano; "sekigaisen kougaku;" (ISBN-13: 987-4885521225); Apr. 1994; pp. 55-56.

* cited by examiner

*Primary Examiner*—David P Porta
*Assistant Examiner*—David S Baker
(74) *Attorney, Agent, or Firm*—Posz Law Group, PLC

(57) ABSTRACT

An infrared gas sensing apparatus for sensing gas includes an infrared source for emitting infrared light, a wavelength tunable filter for selectively allows passage of the infrared light at a specific wavelength, an infrared detector for detecting the amount of the filtered infrared light, and a control circuit for controlling the wavelength tunable filter. The control circuit has a check circuit that checks whether the wavelength tunable filter selects a collect wavelength. The check circuit controls the wavelength tunable filter so that the wavelength tunable filter allows passage of the infrared light at a wavelength within a wavelength range where atmospheric gases do not absorb the infrared light. The check circuit checks whether the wavelength tunable filter operates normally by comparing the amount of the filtered infrared light with a reference value.

9 Claims, 6 Drawing Sheets

INFRARED GAS SENSING APPARATUS AND METHOD

CROSS CHECK TO RELATED APPLICATION

This application is based on and incorporates herein by reference Japanese Patent Application No. 2006-254716 filed on Sep. 20, 2006.

FIELD OF THE INVENTION

The present invention relates to an infrared gas sensing apparatus and method.

BACKGROUND OF THE INVENTION

U.S. Pat. No. 6,590,710 corresponding to JP-A-2001-228326 discloses an infrared gas sensing apparatus for measuring the concentration of a target gas that absorbs a specific wavelength of infrared light. The gas sensing apparatus includes an infrared source that emits the infrared light, a wavelength tunable filter (i.e., Fabry-Perot filter) that selects the specific wavelength of the infrared light, and an infrared detector that detects the filtered infrared light. The gas sensing apparatus measures the concentration of the target gas based on the amount of the infrared light detected by the infrared detector.

Figure 6:
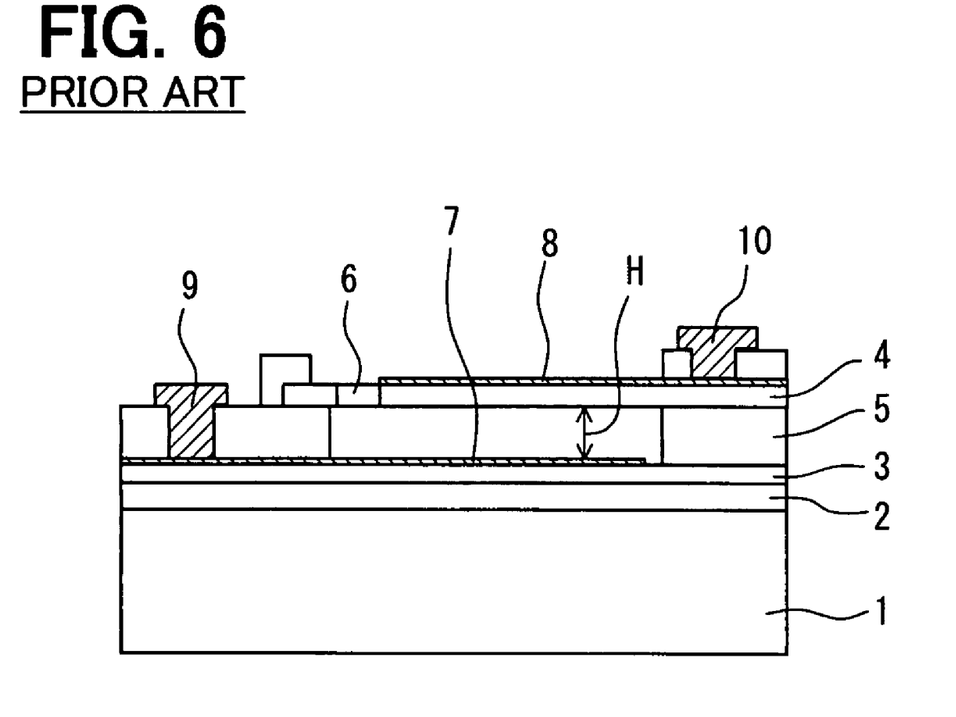
FIG. 6 is a cross-sectional view of a wavelength tunable filter in a conventional infrared gas sensor.

As shown in FIG. 6, the wavelength tunable filter includes a first mirror 3 and a second mirror 4. The first mirror 3 is formed on a silicon substrate 1 through a first oxide film 2. The second mirror 4 is formed on a second oxide film 5, which is formed on the first mirror 3. The first and second mirrors 3, 4 face each other.

A gap H is formed between the first and second mirrors 3, 4 by etching the second oxide film 5 via an etching hole 6. Therefore, the second mirror 4 is displaceable with respect to the first mirror 3 by application of an external force. The gap distance of the gap H is equal to the thickness of the second oxide film 5.

The first and second mirrors 3, 4 are made of polysilicon, for example. The first mirror 3 has a first electrode 7 on one surface. Also, the second mirror 4 has a second electrode 8 on one surface. The first and second electrodes 7, 8 are formed by a highly-concentrated impurity doping applied to the surfaces of the first and second mirrors 3, 4, respectively.

A first external electrode 9 is formed on the first electrode 7 and electrically coupled to the first electrode 7. Also, a second external electrode 10 is formed on the second electrode 8 and electrically coupled to the second electrode 8.

The wavelength tunable filter has a center wavelength $\lambda$ determined by the gap distance of the gap H, i.e., the thickness of the second oxide film 5. For example, the center wavelength $\lambda$ is 3100 nanometers (nm). Since the first mirror 3 serves as a lower mirror of the wavelength tunable filter, the optical thickness needs to be equal to a quarter of the center wavelength $\lambda$. For example, the second oxide film 5 has the thickness of 592 nm and the refractive index of 1.309. Each of the first and second mirrors 3, 4 has the thickness of 248 nm and the refractive index of 3.125.

When a voltage is applied between the first and second electrodes 7, 8 through the first and external electrodes 9, 10, electrostatic attraction force is produced between the first and second electrodes 7, 8. The second electrode 8 is displaced with respect to the first electrode 7 by the electrostatic attraction force. As a result, the gap distance of the gap H is changed. The gap distance is adjusted by adjusting the voltage applied between the first and second electrodes 7, 8. Therefore, the wavelength tunable filter can select the specific wavelength of the infrared light according to the target gas.

In the wavelength tunable filter shown in FIG. 6, the gap distance of the gap H can be adjusted in three levels so that the wavelength tunable filter can select the specific wavelength from three different wavelengths of the infrared light. Thus, the infrared gas sensing apparatus can detect the concentrations of two components of the target gas with one filter. Therefore, the infrared gas sensing apparatus has a small size and is manufactured at low cost.

However, if a foreign matter enters the gap H and is sandwiched between the first and second electrodes 7, 8, the gap distance of the gap H cannot be adjusted. As a result, the infrared gas sensing apparatus incorrectly detects the concentration of the target gas, because the wavelength tunable filter cannot select the specific wavelength where the target gas absorbs the infrared light.

SUMMARY OF THE INVENTION

In view of the above-described problem, it is an object of the present invention to provide an infrared gas sensing apparatus and method for accurately measuring the concentration of a target gas by checking whether a wavelength tunable filter selects a correct wavelength.

A gas sensing apparatus for sensing gas includes an infrared source, a wavelength tunable filter, an infrared detector, a housing, and a control circuit. The gas absorbs infrared light at a first wavelength. The infrared source emits the infrared light. The wavelength tunable filter selectively allows passage of the infrared light at a specific wavelength. The control circuit includes a measurement circuit and a check circuit The measurement circuit controls the wavelength tunable filter, so that the wavelength tunable filter allows passage of the infrared light at the first wavelength and outputs a first filtered infrared light. The check circuit controls the wavelength tunable filter, so that the wavelength tunable filter allows passage of the infrared light at a second wavelength and outputs a second filtered infrared light. The infrared detector detects a first amount of the first filtered infrared light and a second amount of the second filtered light. The infrared light source, the wavelength tunable filter, and the infrared detector are accommodated in the housing. The housing has an inlet for introducing the gas therein.

The measurement circuit calculates concentration of the gas based on the first amount of the first filtered infrared light. The check circuit checks whether the wavelength tunable filter operates normally by comparing the second amount of the second filtered infrared light with a reference value. The second wavelength is within a wavelength range where atmospheric gases do not absorb the infrared light. Due to the check circuit, the gas sensing apparatus can accurately detect the gas. The check circuit checks the wavelength tunable filter based on the transmittance of the infrared light through the atmospheric gases. In other words, the check circuit checks the wavelength tunable filter by using air, not special gas. In such an approach, structure of the gas sensing apparatus can be simplified. Further, because of the simple structure, the gas sensing apparatus can have a small size and be manufactured at low cost.

A method for sensing gas using a wavelength tunable filter includes emitting an infrared light, setting the wavelength tunable filter so that the wavelength tunable filter allows passage of the infrared light at a first wavelength and outputs a first filtered infrared light, detecting a first amount of the first filtered infrared light, and checking whether the wavelength tunable filter operates normally by comparing the first amount with a reference value. The first wavelength is within a wavelength range where atmospheric gases do not absorb the infrared light.

BRIEF DESCRIPTION OF THE DRAWINGS

The above and other objectives, features and advantages of the present invention will become more apparent from the following detailed description made with check to the accompanying drawings. In the drawings.

DETAILED DESCRIPTION OF THE PREFERRED EMBODIMENT

Figure 1:
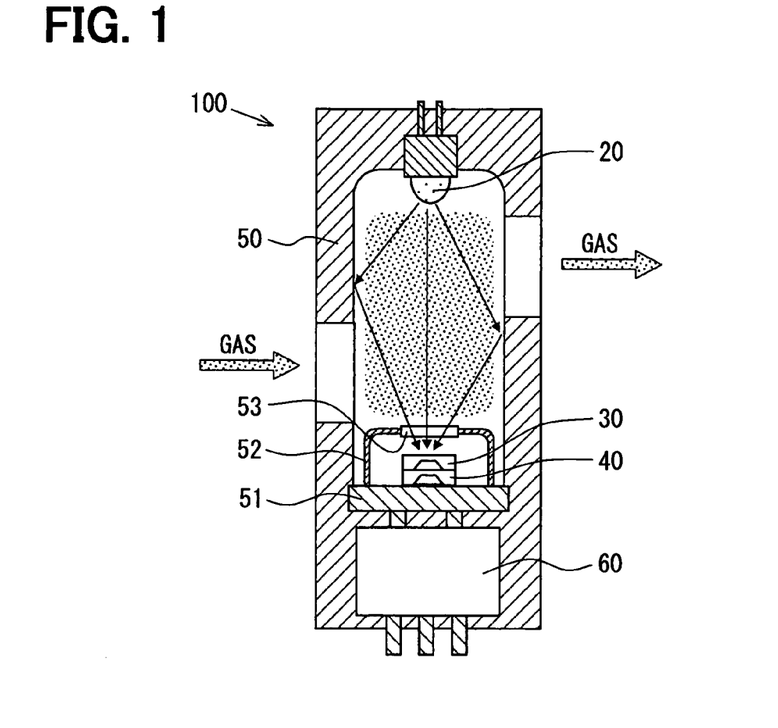
FIG. 1 is a cross-sectional view of an infrared gas sensor according to an embodiment of the present invention.
Figure 2:
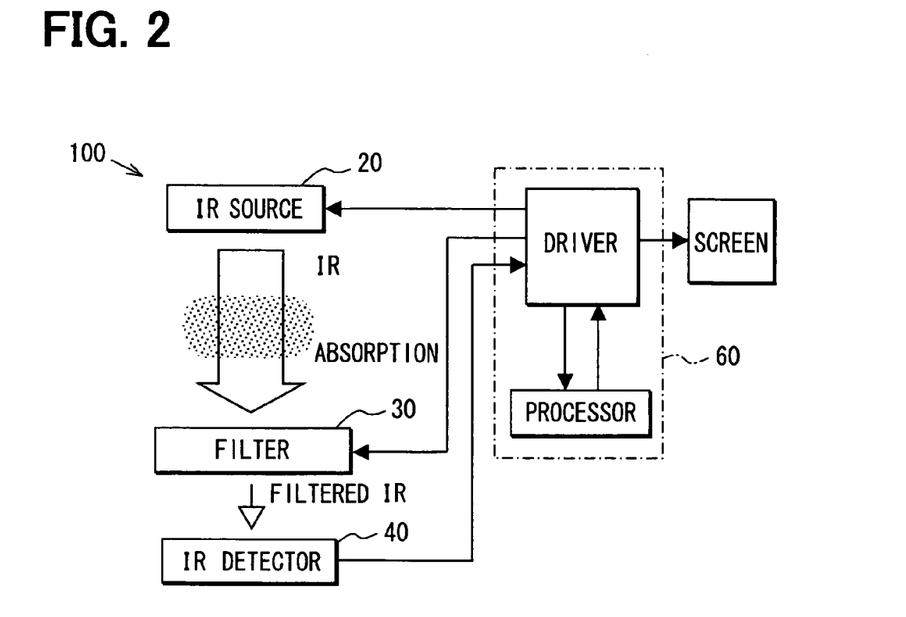
FIG. 2 is a block diagram of the infrared gas sensor of FIG. 1.

As shown in FIGS. 1, 2, an infrared gas sensor 100 according to an embodiment of the present invention includes an infrared (IR) source 20, a wavelength tunable filter 30, an infrared (IR) detector 40, a housing 50, and a control circuit 60. The infrared source 20, the wavelength tunable filter 30, the infrared detector 40, and the control circuit 60 are accommodated in the housing 50.

The infrared source 20 may be, for example, an incandescent lamp. As indicated by arrows in FIG. 1, the infrared source 20 emits infrared light with a continuous range of wavelengths from 2 micrometers (μm) to 10 μm.

The wavelength tunable filter 30 is a Fabry-Perot interference filter. The wavelength tunable filter 30 selects a specific wavelength of the infrared light to be sent to the infrared detector 40 from the infrared source 20. As shown in detail in FIG. 3, the wavelength tunable filter 30 includes a substrate 31, an antireflective film 32 formed on the substrate 31, a first mirror 33 formed on the substrate 31 through the antireflective film 32, and a second mirror 34 formed on the first mirror 33 through a sacrificial layer. The first and second mirrors 33, 34 face each other.

Figure 3:
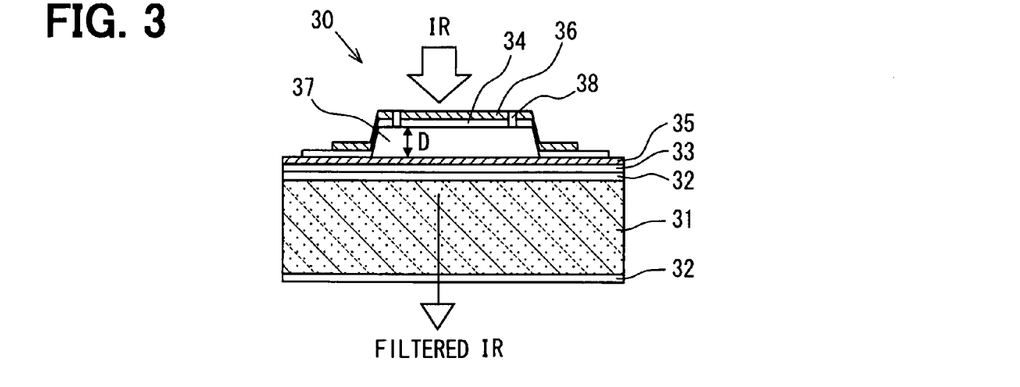
FIG. 3 is a cross-sectional view of a wavelength tunable filter in the infrared gas sensor of FIG. 1.

A gap 37 is formed between the first and second mirrors 33, 34 by etching the sacrificial layer via an etching hole 38. The second mirror 34 can be displaced with respect to the first mirror 33, when external force is applied to the second mirror 34. The first mirror 33 has a first electrode 35 on one surface. The second mirror 34 has a second electrode 36 on one surface. The first and second electrodes 35, 36 may be, for example, formed by a highly-concentrated impurity doping applied to the surfaces of the first and second mirrors 33, 34, respectively. The first and second electrodes 35, 36 face each other.

The substrate 31 may be, for example, made of silicon, quartz, or the like. The first and second mirrors 33, 34 and the first and second electrodes 35, 36 are thin layers and may be, for example, made of molybdenum, silicon, germanium, silicon nitride, oxide silicon, or the like.

Thus, the wavelength tunable filter 30 has a small size and can be manufactured easily by using micro-electro-mechanical systems (MEMS) technology.

In the wavelength tunable filter 30, the infrared light at the specific wavelength equal to a half or quarter of a gap distance D of the gap 37 is multiply reflected between the first and second mirrors 33, 34 so that interference occurs. As a result, the infrared light only at the specific wavelength passes through the wavelength tunable filter 30.

When a voltage is applied between the first and second electrodes 35, 36, electrostatic attraction force is produced between the first and second electrodes 35, 36. The second mirror 34 is displaced with respect to the first mirror 33 by the electrostatic attraction force. The gap distance D of the gap 37 can be steplessly adjusted by adjusting the voltage applied between the first and second electrodes 35, 36. By adjusting the gap distance D, therefore, the wavelength tunable filter 30 can select the specific wavelength of the infrared light to be sent to the infrared detector 40.

The infrared detector 40 detects the filtered infrared light and outputs an electrical signal indicative of the amount of the detected infrared light. The infrared detector 40 may be, for example, a thermopile, a pyroelectric sensor, or the like.

Referring again to FIG. 1, the wavelength tunable filter 30 and the infrared detector 40 are sealed in a container formed with a stem 51 and a case 52 with a transparent window 53. The infrared light emitted by the infrared source 20 enters the wavelength tunable filter 30 through the transparent window 53.

The housing 50 has an inlet and an outlet for a target gas to be detected. The target gas is introduced in a light path between the infrared source 20 and the wavelength tunable filter 30. The target gas at least partially absorbs the specific wavelength of the target gas. The wavelength tunable filter 30 allows the passage of the infrared light only at the specific wavelength.

The filtered infrared light reaches the infrared detector 40 and is converted into the electrical signal. The electrical signal is transmitted to a processor in the control circuit 60, and the processor calculates the concentration of the target gas based on the electrical signal.

As described above, the infrared gas sensor 100 includes the infrared source 20 that emits the infrared light, the wavelength tunable filter 30 that selects the specific wavelength of the infrared light, and the infrared detector 40 that detects the filtered infrared light and converts the detected infrared light into the electrical signal. The specific wavelength selected by the wavelength tunable filter 30 can be steplessly changed by changing the gap distance D of the gap 37 between the first and second mirrors 33, 34. Thus, the infrared gas sensor 100 can detect concentrations of various kinds of gases.

FIGS. 5A-5I are diagrams showing transmittance of infrared light through atmospheric gases. The diagrams are founded in a Japanese book "sekigaisen kougaku" (ISBN-13: 978-4885521225) published by Haruyoshi Hisano in April 1994. As can be seen from FIGS. 5A-5I, the transmittance of infrared light is approximately 100 percent in wavelength ranges between 1.55 micrometers (μm) and 1.75 μm, between 2.05 μm and 2.33 μm, between 3.5 μm and 4.16 μm, and between 9.4 μm and 12.4 μm. The control circuit 60 may have filter check circuit for checking, based on the transmittance of infrared light through the atmospheric gases, whether the wavelength tunable filter 30 operates normally. The wavelength ranges, where the transmittance of infrared light is approximately 100 percent, are hereinafter called "non-absorption wavelength range". Wavelength ranges outside the non-absorption wavelength range are hereinafter called "absorption wavelength range".

Figure 4:
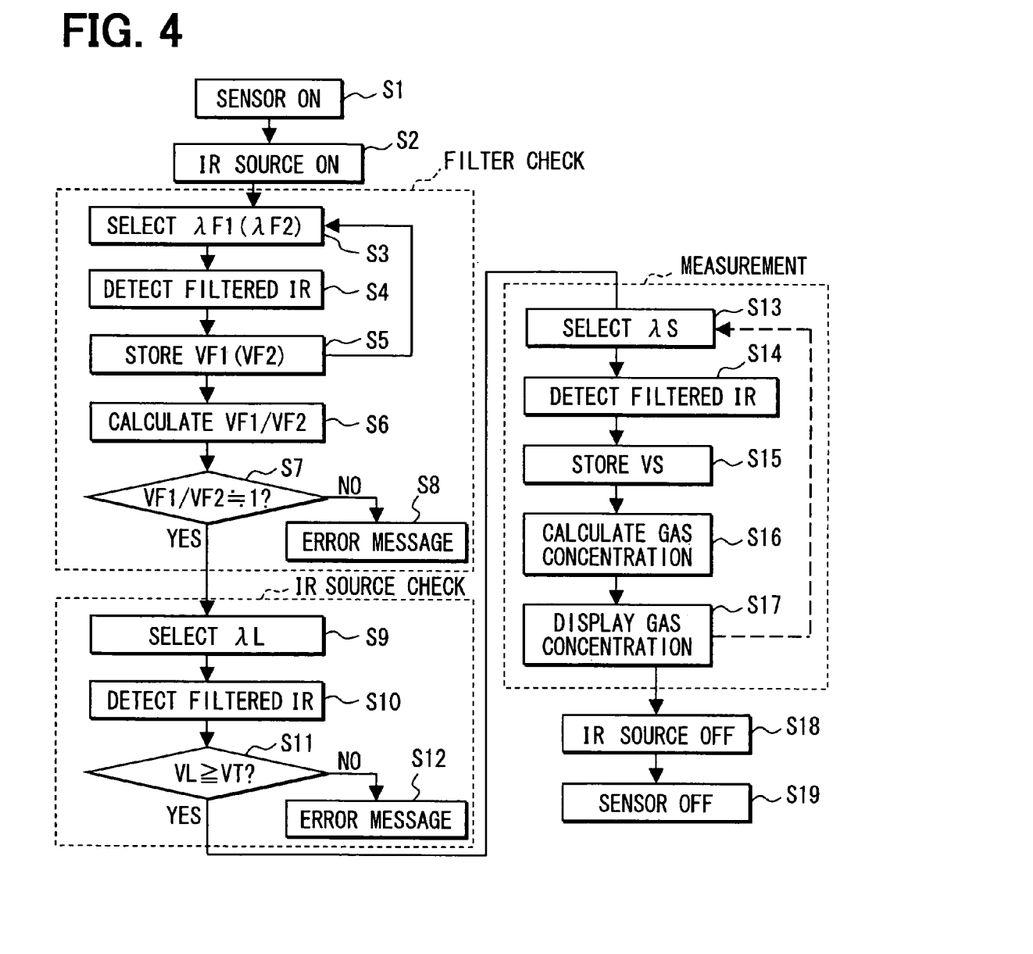
FIG. 4 is a flow chart of the infrared gas sensor of FIG. 1.
Figure 5A:
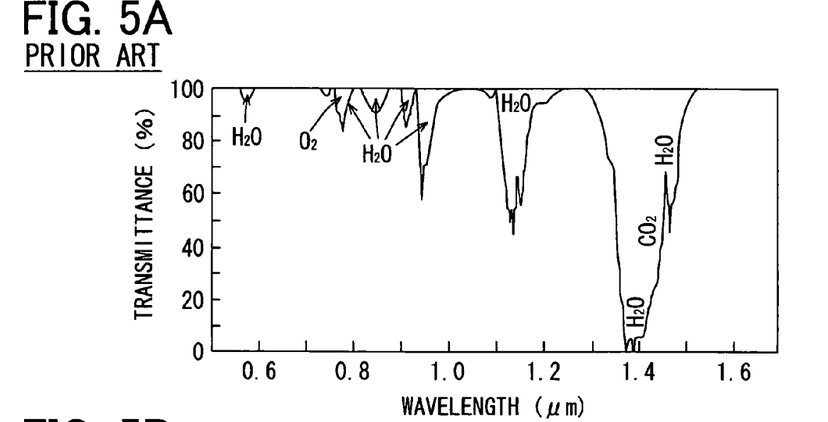
FIGS. 5A-5I are diagrams showing transmittance of infrared light through the atmospheric gases.
Figure 5B:
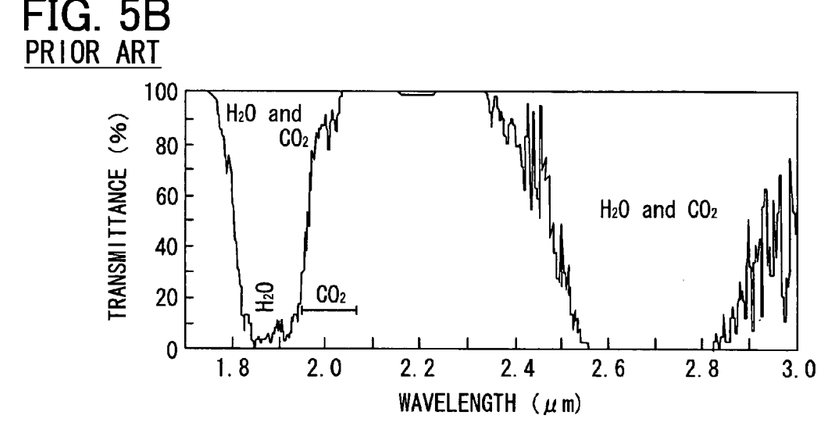
Figure 5C:
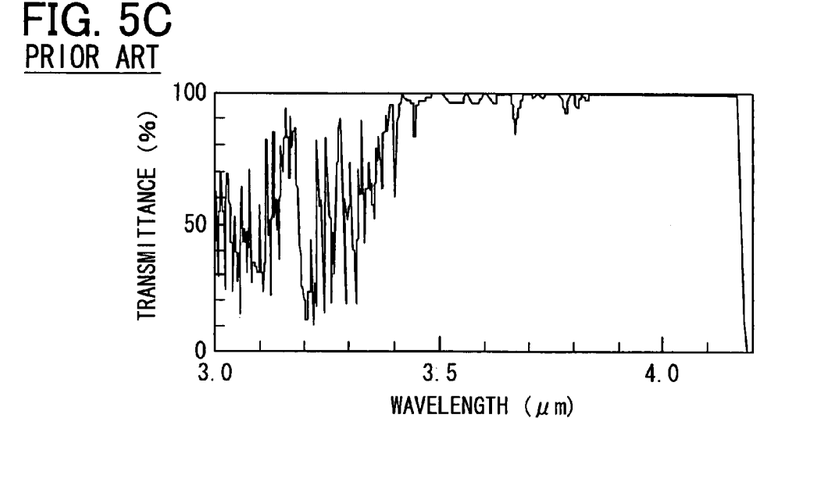
Figure 5D:
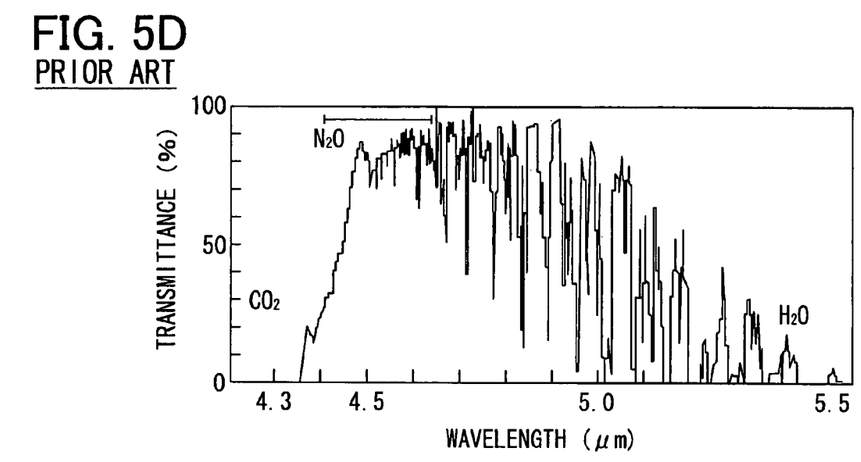
Figure 5E:
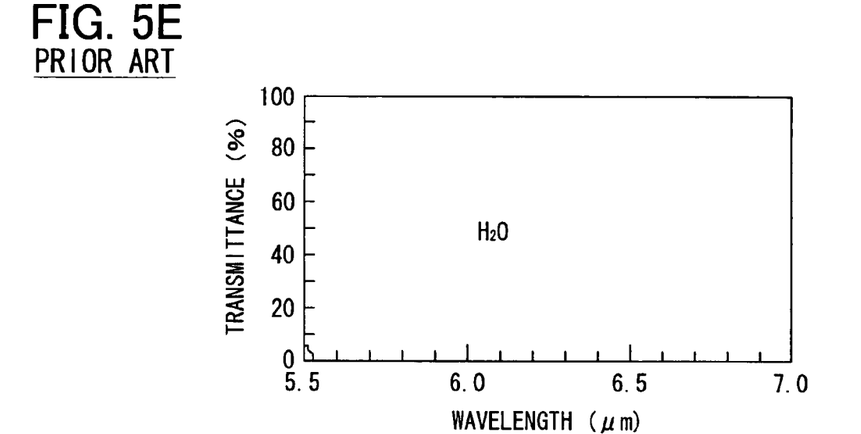
Figure 5F:
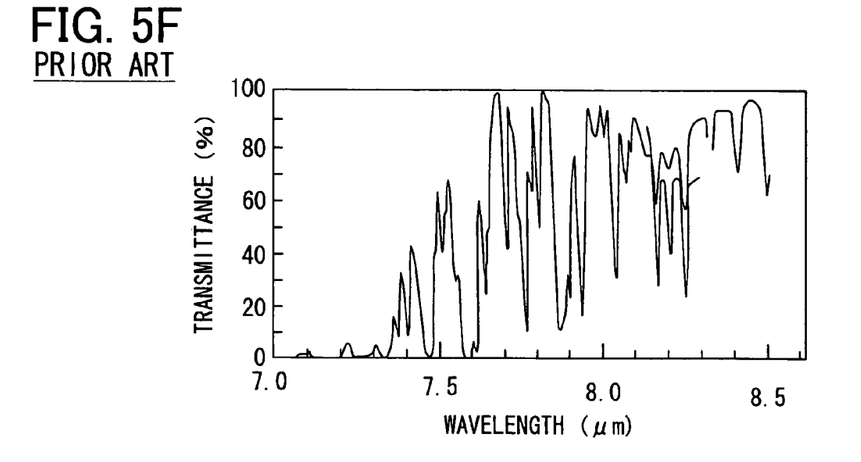
Figure 5G:
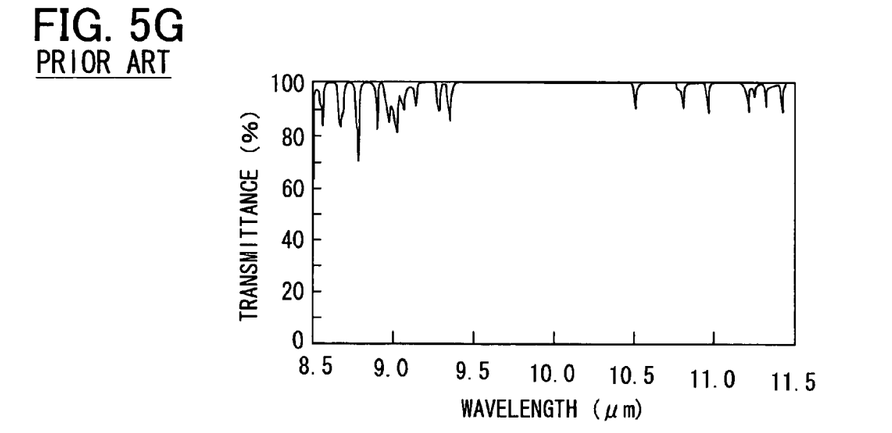
Figure 5H:
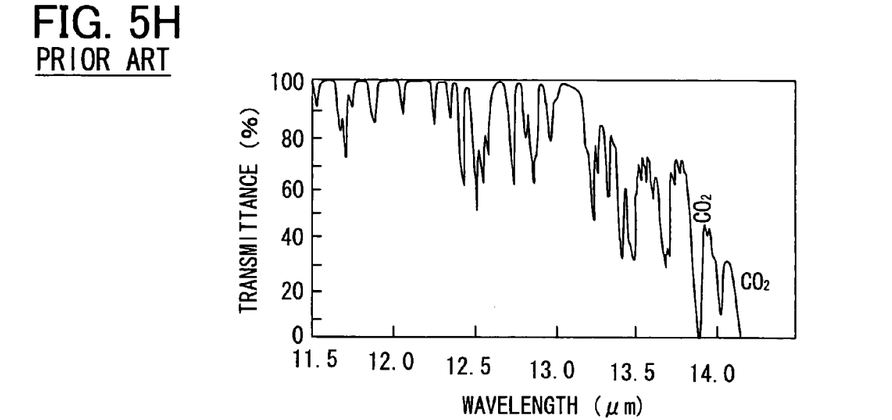
Figure 5I:
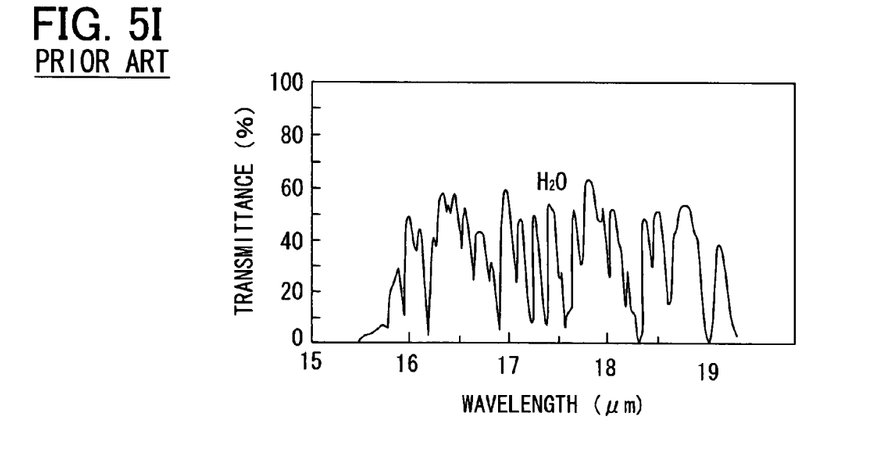

The infrared gas sensor 100 operates according to a flow chart of FIG. 4. At step S1, the infrared gas sensor 100 is powered on. Then, at step S2, the infrared source 20 is powered on by a driver in the control circuit 60 and emits infrared light.

Then, at step S3, the gap distance D of the wavelength tunable filter 30 is adjusted so that the wavelength tunable filter 30 selects a first check wavelength λF1 within the non-absorption wavelength range. For example, the first check wavelength λF1 is 2.1 μm. Then, at step S4, the infrared detector 40 detects the filtered infrared light and converts the detected infrared light into a first check signal VF1 indicative of the amount of the detected infrared light. Then, at step S5, the first check signal VF1 is stored in a memory (not shown) in the control circuit 60.

The steps S3-S5 are repeated one more time. At the second step S3, the gap distance D of the wavelength tunable filter 30 is adjusted so that the wavelength tunable filter 30 selects a second check wavelength λF2 within the non-absorption wavelength range. The second check wavelength λF2 is different from the first check wavelength λF1. For example, the second check wavelength λF2 is 2.3 μm. In this case, the second check wavelength λF2 is within the same non-absorption wavelength range as the first check wavelength λF1. Alternatively, the second check wavelength λF2 may be within the different non-absorption wavelength range from the first check wavelength λF1. For example, the second check wavelength λF2 may be within the wavelength range between 9.4 μm and 12.4 μm. Then, at the second step S4, the infrared detector 40 detects the filtered infrared light and converts the detected infrared light into a second check signal VF2 indicative of the amount of the detected infrared light. Then, at the second step S5, the second check signal VF2 is stored in the memory in the control circuit 60.

Then, at step S6, the control circuit 60 calculates a signal ratio VF1/VF2 between the first check signal VF1 and the second check signal VF2. Then, at step S7, the control circuit 60 determines whether the signal ratio VF1/VF2 is approximately one. Since the first check wavelength λF1 and the second check wavelength λF2 are approximately the same and within the non-absorption wavelength, the first check signal VF1 and the second check signal VF2 are approximately the same. Therefore, the signal ratio VF1/VF2 becomes approximately one, unless the wavelength tunable filter 30 malfunctions.

At step S7, if the signal ratio VF1/VF2 is not approximately one, the control circuit 60 determines that the wavelength tunable filter 30 malfunctions and selects an incorrect wavelength i.e., a wavelength other than the first check wavelength λF1 and the second check wavelength λF2. Therefore, at step S8, a first error message, indicating that the wavelength tunable filter 30 malfunctions, appears on a screen shown in FIG. 2, and the process is stopped.

In contrast, at step S7, if the signal ratio VF1/VF2 is approximately one, the control circuit 60 determines that the wavelength tunable filter 30 operates normally. Therefore, the process is continued.

Then, at step S9, the gap distance D of the wavelength tunable filter 30 is adjusted so that the wavelength tunable filter 30 selects a third check wavelength λL. Then, at step S10, the infrared detector 40 detects the filtered infrared light and converts the detected infrared light into a third check signal VL indicative of the amount of the detected infrared light. Then, at step S11, the control circuit 60 determines whether the third check signal VL exceeds a threshold value VT.

At step S11, if the third check signal VL is less than the threshold value VT, the control circuit 60 determines that the amount of the infrared light emitted by the infrared source 20 is reduced due to, for example, age deterioration. Therefore, at step S12, a second error message, indicating that the infrared source 20 malfunctions, appears on the screen, and the process is stopped.

In contrast, at step S11, if the third check signal VL exceeds the threshold value VT, the control circuit 60 determines that the infrared source 20 operates normally. Therefore, the process is continued.

Then, at step S13, the gap distance D of the wavelength tunable filter 30 is adjusted so that the wavelength tunable filter 30 selects a target wavelength λS where the target gas to be sensed absorbs the infrared light. Then, at step S14, the infrared detector 40 detects the filtered infrared light and converts the detected infrared light into a detection signal VS indicative of the detected infrared light. Then, at step S15, the detection signal VS is stored in the memory in the control circuit 60. Then, at step S16, the control circuit 60 calculates the concentration of the target gas based on the detection signal VS. Then, at step S17, the calculated concentration appears on the screen. If there is a need to detect concentrations of a plurality of components of the target gas, steps S13-S17 are repeated.

Then, at step S18, the infrared source 20 is powered off. Then, at step S19, the infrared gas sensor 100 is powered off. In the flow chart of FIG. 4, the steps S3-S8 correspond to a filter check process for checking whether the wavelength tunable filter 30 operates normally, the steps S9-S12 correspond to an infrared source check process for checking whether the infrared source 20 operates normally, and the steps S13-S17 correspond to a measurement process for measuring the concentration of the target gas.

As described above, according to the infrared gas sensor 100, the filter check process is performed before the measurement process is performed. In the filter check process, the amount of the filtered infrared light at the first and second check wavelengths λF1, λF2 within the non-absorption wavelength range is detected and converted into the first and second check signals VF1, VF2, respectively. The malfunction of the wavelength tunable filter 30 is checked based on the signal ratio VF1/VF2. In such an approach, the malfunction of the wavelength tunable filter 30, can be detected, even if the amount of the infrared light emitted by the infrared source 20 is reduced due to the deterioration.

The malfunction of the wavelength tunable filter 30 is checked based on the transmittance of the infrared light through the atmospheric gases. In other words, the malfunction of the wavelength tunable filter 30 is checked by using air, not special gas. Therefore, structure of the infrared gas sensor 100 can be simplified so that the wavelength tunable filter 30 can be easily checked in a short time. Further, because of the simple structure, the infrared gas sensor 100 can have a small size and be manufactured at low cost.

It is preferable that the first and second check wavelengths λF1, λF2 should be near the border of the non-absorption wavelength range. It is more preferable that the non-absorption range be bounded by the first and second check wavelengths λF1, λF2. In such an approach, even if the wavelength tunable filter 30 malfunctions slightly, the wavelength tunable filter 30 allows passage of the infrared light at a wavelength outside the non-absorption wavelength range, i.e., within the absorption wavelength range. As a result, although the wavelength tunable filter 30 malfunctions slightly, the signal ratio VF1/VF2 significantly deviates from one. Therefore, the malfunction of the wavelength tunable filter 30 can be surely detected so that the concentration of the target gas can be accurately measured.

Alternatively, a reference signal V0 corresponding to a reference wavelength λF0 within the non-absorption wavelength range may be prestored in the memory in the control circuit 60. In this case, the wavelength tunable filter 30 is checked as follows. In the filter check process, the gap distance D of the wavelength tunable filter 30 is adjusted so that the wavelength tunable filter 30 selects the reference wavelength λF0. Then, the infrared detector 40 detects the filtered infrared light and converts the detected infrared light into a reference signal VF0 indicative of the amount of the detected infrared light. The wavelength tunable filter 30 is checked based on a signal ratio VF0/V0. In such an approach, the filter check process can be simplified.

In addition to the filter check process, the infrared light source check process is performed before the measurement process is performed. In such an approach, the malfunction of the infrared source 20 can be detected so that the concentration of the target gas can be measured more accurately.

As described above, the infrared gas sensor 100 according to the embodiment has a small size and is manufactured at low cost. Further, the infrared gas sensor 100 can measure the concentrations of many components of the target gas by using the wavelength tunable filter 30. Furthermore, the malfunctions of the infrared source 20 and the wavelength tunable filter 30 are detected so that the concentrations can be accurately measured. Therefore, the infrared gas sensor 100 can be used even under severe conditions.

For example, the infrared gas sensor 100 may be mounted to a vehicle to measure an exhaust gas of the vehicle. The exhaust gas mainly contains COx, NOx, and SOx. These main components of the exhaust gas absorb infrared light at a wavelength between 3 μm and 8 μm. Therefore, when the infrared gas sensor 100 is used to measure the exhaust gas of the vehicle, it is preferable that the wavelength tunable filter 30 be checked by using the wavelength ranges between 2.05 μm and 2.33 μm, and between 9.4 μm and 12.4 μm, each of which is the non-absorption wavelength range and located next to the wavelength range between 3 μm and 8 μm, where the exhaust gas absorb infrared light. In such an approach, the infrared gas sensor 100 can accurately measure the concentrations of the components of the exhaust gas.

(Modifications)

The embodiment described above may be modified in various ways. For example, the steps S3-S5 may be repeated two or more times so that the malfunction of the wavelength tunable filter 30 can be more surely detected.

In the above described embodiment, the filter check process is performed each time the infrared gas sensor 100 is powered on, i.e., the wavelength tunable filter 30 is powered on. Alternatively, the filter check process may be performed each time step S17 is completed, i.e., one component of the target gas is measured. In such an approach, the infrared gas sensor 100 can measure the concentration of the target gas more accurately.

Such changes and modifications are to be understood as being within the scope of the present invention as defined by the appended claims.

What is claimed is:

1. A gas sensing apparatus for sensing gas that absorbs infrared light at a first wavelength, the gas sensing apparatus comprising:
   an infrared source that emits the infrared light;
   a wavelength tunable filter that selectively allows passage of the infrared light at a specific wavelength;
   a control circuit that includes a measurement circuit and a check circuit, the measurement circuit controlling the wavelength tunable filter, so that the wavelength tunable filter allows passage of the infrared light at the first wavelength and outputs a first filtered infrared light, the check circuit controlling the wavelength tunable filter, so that the wavelength tunable filter allows passage of the infrared light at a second wavelength and outputs a second filtered infrared light;
   an infrared detector that detects a first amount of the first filtered infrared light and a second amount of the second filtered light; and
   a housing for accommodating the infrared light source, the wavelength tunable filter, and the infrared detector, the housing having an inlet for introducing the gas therein, wherein
   the measurement circuit calculates concentration of the gas based on the first amount of the first filtered infrared light,
   the check circuit checks whether the wavelength tunable filter operates normally by comparing the second amount of the second filtered infrared light with a reference value,
   the second wavelength is within a wavelength range where atmospheric gases do not absorb the infrared light,
   the check circuit controls the wavelength tunable filter, so that the wavelength tunable filter allows passage of the infrared light at a third wavelength and outputs a third filtered infrared light, the third wavelength being within the wavelength range,
   the infrared detector detects a third amount of the third filtered infrared light as the reference value, and,
   the check circuit calculates a ratio between the second amount and the third amount and checks whether the wavelength tunable filter operates normally based on a deviation of the ratio from one.

2. The gas sensing apparatus according to claim 1, wherein the wavelength range is bounded by the second wavelength and the third wavelength.

3. The gas sensing apparatus according to claim 1, wherein the wavelength range is between 1.55 micrometers and 1.75 micrometers, between 2.05 micrometers and 2.33 micrometers, between 3.5 micrometers and 4.16 micrometers, or between 9.4 micrometers and 12.4 micrometers.

4. The gas sensing apparatus according to claim 1, wherein
   the wavelength tunable filter is a Fabry-Perot filter and includes a substrate, a first mirror formed on the substrate, and a second mirror that faces and is spaced from the first mirror by a predetermined distance,
   the first mirror has a first electrode,
   the second mirror has a second electrode that faces the first electrode, the second mirror being displaceable with respect to the first mirror by application of a voltage between the first electrode and the second electrode, and
   the control circuit controls the wavelength tunable filter by adjusting the voltage applied between the first electrode and the second electrode, so that the wavelength tunable filter selectively allows passage of the infrared light at the specific wavelength.

5. The gas sensing apparatus according to claim 1, wherein the gas is an exhaust gas of a vehicle.

6. A method for sensing gas using a wavelength tunable filter, the method comprising:
   emitting an infrared light;
   setting the wavelength tunable filter so that the wavelength tunable filter allows passage of the infrared light at a first wavelength and outputs a first filtered infrared light;
   detecting a first amount of the first filtered infrared light;

checking whether the wavelength tunable filter operates normally by comparing the first amount with a reference value;

setting the wavelength tunable filter so that the wavelength tunable filter allows passage of the infrared light at a second wavelength and outputs a second filtered infrared light; and detecting a second amount of the second filtered light as the reference value, wherein each of the first wavelength and the second wavelength is within a wavelength range where atmospheric gases do not absorb the infrared light, wherein the method further includes calculating a ratio between the first amount and the second amount, and a deviation of the ratio from one, and wherein the checking step checks whether the wavelength tunable filter operates normally based on the deviation.

7. The method according to claim 6, wherein the wavelength range is bounded by the first wavelength and the second wavelength.

8. The method according to claim 6, wherein
the gas is an exhaust gas of a vehicle, and
the wavelength range is between 2.05 micrometers and 2.33 micrometers, and between 9.4 micrometers and 12.4 micrometers.

9. The method according to claim 6, wherein the checking step is performed each time the wavelength tunable filter is powered on.

* * * * *